United States Patent
Nebhani et al.

(10) Patent No.: US 8,993,669 B2
(45) Date of Patent: Mar. 31, 2015

(54) FUNCTIONALIZED POLYMER, RUBBER COMPOSITION AND PNEUMATIC TIRE

(75) Inventors: Leena Nebhani, Copley, OH (US); Michael Joseph Rachita, North Canton, OH (US)

(73) Assignee: The Goodyear Tire & Rubber Company, Akron, OH (US)

( * ) Notice: Subject to any disclaimer, the term of this patent is extended or adjusted under 35 U.S.C. 154(b) by 530 days.

(21) Appl. No.: 13/432,375

(22) Filed: Mar. 28, 2012

(65) Prior Publication Data

US 2013/0261252 A1 Oct. 3, 2013

(51) Int. Cl.
| | |
|---|---|
| C08F 36/04 | (2006.01) |
| C07F 7/18 | (2006.01) |
| C08C 19/20 | (2006.01) |
| C08C 19/22 | (2006.01) |
| C08C 19/25 | (2006.01) |
| C08K 5/548 | (2006.01) |
| C08L 9/06 | (2006.01) |
| B60C 1/00 | (2006.01) |
| C08F 2/38 | (2006.01) |

(52) U.S. Cl.
CPC ............... *C08F 36/04* (2013.01); *C07F 7/1836* (2013.01); *C08C 19/20* (2013.01); *C08C 19/22* (2013.01); *C08C 19/25* (2013.01); *C08K 5/548* (2013.01); *C08L 9/06* (2013.01); *B60C 1/00* (2013.01); *C08F 2/38* (2013.01)
USPC ..... 524/492; 524/572; 525/332.9; 525/333.1; 525/333.2

(58) Field of Classification Search
USPC .......... 524/492, 572; 525/332.9, 333.1, 333.2
See application file for complete search history.

(56) References Cited

U.S. PATENT DOCUMENTS

| | | | | |
|---|---|---|---|---|
| 4,421,893 | A | * 12/1983 | Haluska et al. | 524/588 |
| 6,127,468 | A | 10/2000 | Cruse et al. | 524/225 |
| 6,229,036 | B1 | 5/2001 | Batz-Sohn et al. | 556/426 |
| 7,781,606 | B2 | 8/2010 | Cruse et al. | 556/429 |
| 8,053,512 | B2 | 11/2011 | Thiele et al. | 524/571 |
| 2010/0087612 | A1 | 4/2010 | Montoya-Goni et al. | |
| 2011/0082253 | A1 | 4/2011 | Thiele et al. | 11/524 |
| 2011/0301261 | A1 | 12/2011 | Thiele et al. | |

FOREIGN PATENT DOCUMENTS

JP 2006176683 * 7/2006 ............. C08L 63/00

OTHER PUBLICATIONS

EPO Search Report dated Aug. 5, 2013.
Styron Synthetic Rubber Technical Information; Jul. 20, 2010, Sprintan SLR 4602—Schkopau, Solution Styrene Butadiene Rubber (S-SBR), pp. 1-3.

* cited by examiner

*Primary Examiner* — Ling Choi
*Assistant Examiner* — Chun-Cheng Wang
(74) *Attorney, Agent, or Firm* — John D. DeLong

(57) ABSTRACT

The present invention is directed to a functionalized elastomer comprising the reaction product of a living anionic elastomeric polymer and a polymerization terminator of formula I

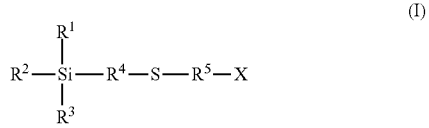

wherein $R^1$, $R^2$, $R^3$, $R^4$, and $R^5$ are as defined. The invention is further directed to a rubber composition including the functionalized elastomer, and a pneumatic tire including the rubber composition.

11 Claims, 8 Drawing Sheets

FUNCTIONALIZED POLYMER, RUBBER COMPOSITION AND PNEUMATIC TIRE

BACKGROUND OF THE INVENTION

In recent years, there is a growing demand for functionalized polymers. Functionalized polymers can be synthesized through various living/controlled polymerization techniques. In the living polymerization process based on active carbanionic center, metals from Groups I and II of the periodic table are commonly used to initiate the polymerization of monomers into polymers. For example, lithium, barium, magnesium, sodium, and potassium are metals that are frequently utilized in such polymerizations. Initiator systems of this type are of commercial importance because they can be used to produce stereo regulated polymers. For instance, lithium initiators can be utilized to initiate the anionic polymerization of isoprene into synthetic polyisoprene rubber or to initiate the polymerization of 1,3-butadiene into polybutadiene rubber having the desired microstructure.

The polymers formed in such polymerizations have the metal used to initiate the polymerization at the growing end of their polymer chains and are sometimes referred to as living polymers. They are referred to as living polymers because their polymer chains which contain the terminal metal initiator continue to grow or live until all of the available monomer is exhausted. Polymers that are prepared by utilizing such metal initiators normally have structures which are essentially linear and normally do not contain appreciable amounts of branching.

This invention details synthesis of functionalized polymers and their use in rubber formulation and tire materials. In general to achieve the best tire performance properties functionalized polymers are highly desirable. In order to reduce the rolling resistance and to improve the tread wear characteristics of tires, functionalized elastomers having a high rebound physical property (low hysteresis) have been used for the tire tread rubber compositions. However, in order to increase the wet skid resistance of a tire tread, rubbery polymers that have a relatively lower rebound physical property (higher hysteresis) which thereby undergo a greater energy loss, have sometimes been used for such tread rubber compositions. To achieve such relatively inconsistent viscoelastic properties for the tire tread rubber compositions, blends (mixtures) of various types of synthetic and natural rubber can be utilized in tire treads.

Functionalized rubbery polymers made by living polymerization techniques are typically compounded with sulfur, accelerators, antidegradants, a filler, such as carbon black, silica or starch, and other desired rubber chemicals and are then subsequently vulcanized or cured into the form of a useful article, such as a tire or a power transmission belt. It has been established that the physical properties of such cured rubbers depend upon the degree to which the filler is homogeneously dispersed throughout the rubber. This is in turn related to the level of affinity that filler has for the particular rubbery polymer. This can be of practical importance in improving the physical characteristics of rubber articles which are made utilizing such rubber compositions. For example, the rolling resistance and traction characteristics of tires can be improved by improving the affinity of carbon black and/or silica to the rubbery polymer utilized therein. Therefore, it would be highly desirable to improve the affinity of a given rubbery polymer for fillers, such as carbon black and silica.

In tire tread formulations, better interaction between the filler and the rubbery polymer results in lower hysteresis and consequently tires made with such rubber formulations have lower rolling resistance. Low tan delta values at 60° C. are indicative of low hysteresis and consequently tires made utilizing such rubber formulations with low tan delta values at 60° C. normally exhibit lower rolling resistance. Better interaction between the filler and the rubbery polymer in tire tread formulations also typically results higher tan delta values at 0° C. which is indicative of better traction characteristics.

The interaction between rubber and carbon black has been attributed to a combination of physical absorption (van der Waals force) and chemisorption between the oxygen containing functional groups on the carbon black surface and the rubber (see D. Rivin, J. Aron, and A. Medalia, Rubber Chem. & Technol. 41, 330 (1968) and A. Gessler, W. Hess, and A Medalia, Plast. Rubber Process, 3, 141 (1968)). Various other chemical modification techniques, especially for styrene-butadiene rubber made by solution polymerization (S-SBR), have also been described for reducing hysteresis loss by improving polymer-filler interactions. In one of these techniques, the solution rubber chain end is modified with aminobenzophenone. This greatly improves the interaction between the polymer and the oxygen-containing groups on the carbon black surface (see N. Nagata, Nippon Gomu Kyokaishi, 62, 630 (1989)). Tin coupling of anionic solution polymers is another commonly used chain end modification method that aids polymer-filler interaction supposedly through increased reaction with the quinone groups on the carbon black surface. The effect of this interaction is to reduce the aggregation between carbon black particles which in turn, improves dispersion and ultimately reduces hysteresis.

SUMMARY OF THE INVENTION

The subject invention provides a low cost means for the end-group functionalization of rubbery living polymers to improve their affinity for fillers, such as carbon black and/or silica. Such functionalized polymers can be beneficially used in manufacturing tires and other rubber products where improved polymer/filler interaction is desirable. In tire tread compounds this can result in lower polymer hysteresis which in turn can provide a lower level of tire rolling resistance.

The present invention is directed to a functionalized elastomer comprising the reaction product of a living anionic elastomeric polymer and a polymerization terminator of formula I

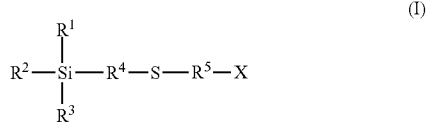

wherein:

$R^1$, $R^2$ and $R^3$ are independently C1 to C8 alkyl or C1 to C8 alkoxy with the proviso that at least two of $R^1$, $R^2$ and $R^3$ are C1 to C8 alkoxy;

$R^4$ is C1 to C8 alkanediyl, C1 to C8 arylene, C1 to C8 alkylarylene, or C1 to C8 arylalkanediyl; Si is silicon; S is sulfur;

X is —O—$R^6$ or

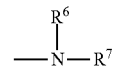

wherein O is oxygen; N is nitrogen; and i) $R^5$ is —$(CH_2)_2$—C(=O)— wherein the $(CH_2)_2$ group is adjacent to the sulfur and $R^6$ and $R^7$ are independently hydrogen or C1 to C8 alkyl, C1 to C8 aryl, C1 to C8 alkylaryl, or C1 to C8 arylalkyl; or ii) $R^5$ and $R^6$ taken together with the heteroatom nitrogen or heteroatom oxygen to which both $R^5$ and $R^6$ are attached form a 5 membered ring wherein $R^5$ is —CH—C(=O)— wherein the carbonyl group is adjacent to the heteroatom and $R^6$ is —$CH_2$—C(=O)— wherein the carbonyl group is adjacent to the heteroatom and $R^7$ is hydrogen or C1 to C8 alkyl, C1 to C8 aryl, C1 to C8 alkylaryl, or C1 to C8 arylalkyl.

The invention is further directed to a rubber composition comprising the functionalized elastomer, and a pneumatic tire comprising the rubber composition.

DETAILED DESCRIPTION OF THE INVENTION

Figure 1:
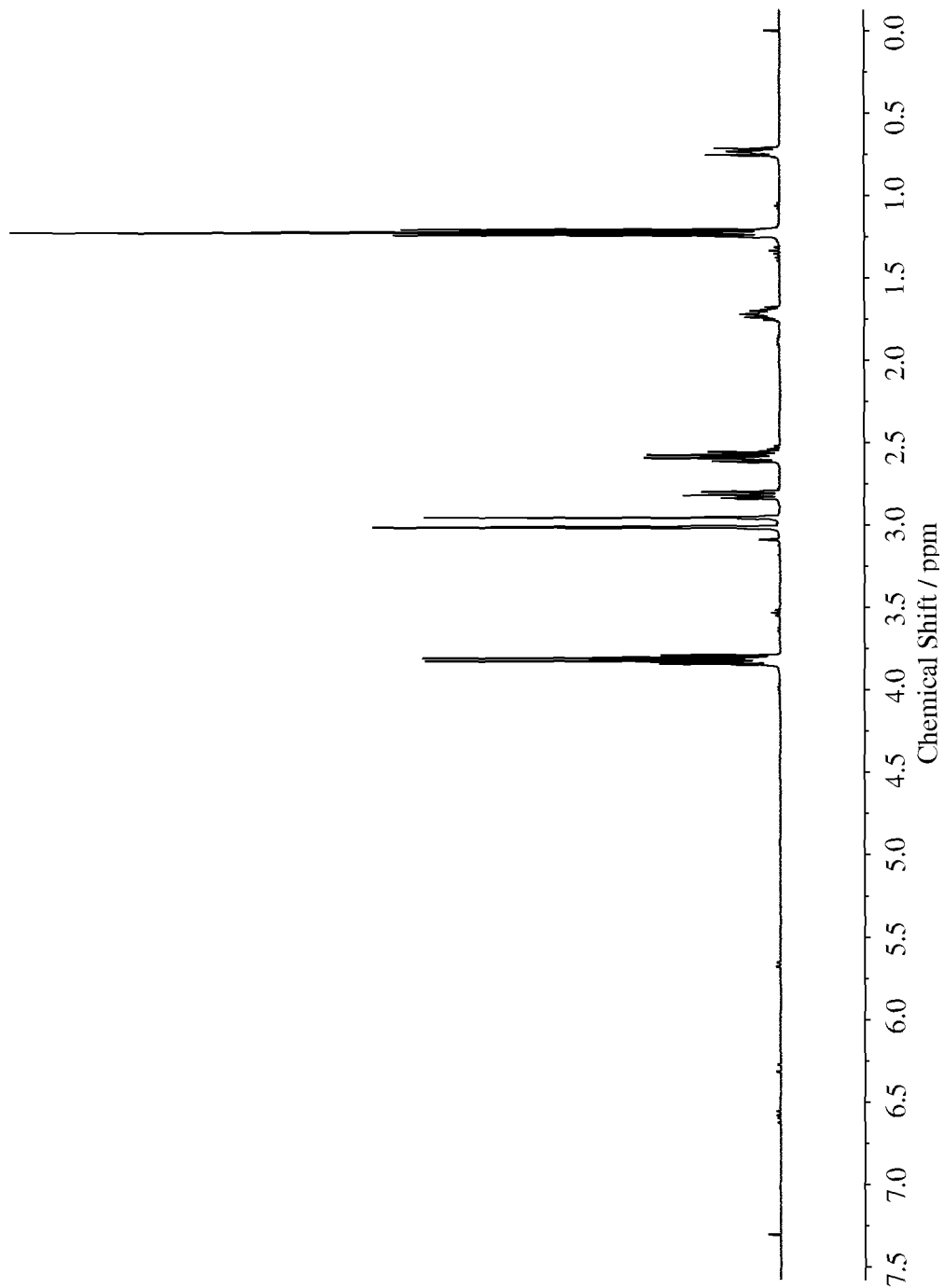
FIG. 1 shows the $^1$H NMR of propanamide, N,N-dimethyl-3-[[3-(triethoxysilyl)propyl]thiol]-.

There is disclosed a functionalized elastomer comprising the reaction product of a living anionic elastomeric polymer and a polymerization terminator of formula I

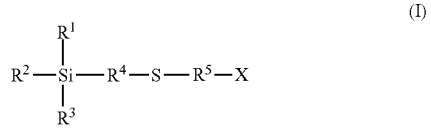

wherein:

$R^1$, $R^2$ and $R^3$ are independently C1 to C8 alkyl or C1 to C8 alkoxy with the proviso that at least two of $R^1$, $R^2$ and $R^3$ are C1 to C8 alkoxy;

$R^4$ is C1 to C8 alkanediyl, C1 to C8 arylene, C1 to C8 alkylarylene, or C1 to C8 arylalkanediyl; Si is silicon; S is sulfur;

X is —O—$R^6$ or

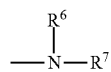

wherein O is oxygen; N is nitrogen; and i) $R^5$ is —$(CH_2)_2$—C(=O)— wherein the $(CH_2)_2$ group is adjacent to the sulfur and $R^6$ and $R^7$ are independently hydrogen or C1 to C8 alkyl, C1 to C8 aryl, C1 to C8 alkylaryl, or C1 to C8 arylalkyl; or ii) $R^5$ and $R^6$ taken together with the heteroatom nitrogen or heteroatom oxygen to which both $R^5$ and $R^6$ are attached form a 5 membered ring wherein $R^5$ is —CH—C(=O)— wherein the carbonyl group is adjacent to the heteroatom and $R^6$ is —$CH_2$—C(=O)— wherein the carbonyl group is adjacent to the heteroatom and $R^7$ is hydrogen or C1 to C8 alkyl, C1 to C8 aryl, C1 to C8 alkylaryl, or C1 to C8 arylalkyl.

There is further disclosed a rubber composition comprising the functionalized elastomer, and a pneumatic tire comprising the rubber composition.

The subject invention provides a means for the end-group functionalization of rubbery living polymers to improve their affinity for fillers, such as carbon black and/or silica. The process of the present invention can be used to functionalize any living polymer which is terminated with a metal of group I or II of the periodic table. These polymers can be produced utilizing techniques that are well known to persons skilled in the art. The metal terminated rubbery polymers that can be functionalized with a terminator of formula I in accordance with this invention can be made utilizing monofunctional initiators having the general structural formula P-M, wherein P represents a polymer chain and wherein M represents a metal of group I or II. The metal initiators utilized in the synthesis of such metal terminated polymers can also be multifunctional organometallic compounds. For instance, difunctional organometallic compounds can be utilized to initiate such polymerizations. The utilization of such difunctional organometallic compounds as initiators generally results in the formation of polymers having the general structural formula M-P-M, wherein P represents a polymer chain and wherein M represents a metal of group I or II. Such polymers which are terminated at both of their chain ends with a metal from group I or II also can be reacted with terminator of formula I to functionalize both of their chain ends. It is believed that utilizing difunctional initiators so that both ends of the polymers chain can be functionalized with the terminator of formula I can further improve interaction with fillers, such as carbon black and silica.

The initiator used to initiate the polymerization employed in synthesizing the living rubbery polymer that is functionalized in accordance with this invention is typically selected from the group consisting of barium, lithium, magnesium, sodium, and potassium. Lithium and magnesium are the metals that are most commonly utilized in the synthesis of such metal terminated polymers (living polymers). Normally, lithium initiators are more preferred.

Organolithium compounds are the preferred initiators for utilization in such polymerizations. The organolithium compounds which are utilized as initiators are normally organo monolithium compounds. The organolithium compounds which are preferred as initiators are monofunctional compounds which can be represented by the formula: R—Li, wherein R represents a hydrocarbyl radical containing from 1 to about 20 carbon atoms. Generally, such monofunctional organolithium compounds will contain from 1 to about 10 carbon atoms. Some representative examples of preferred butyllithium, secbutyllithium, n-hexyllithium, n-octyllithium, tertoctyllithium, n-decyllithium, phenyllithium, 1-naphthyllithium, 4-butylphenyllithium, p-tolyllithium, 4-phenylbutyllithium, cyclohexyllithium, 4-butylcyclohexyllithium, and 4-cyclohexylbutyllithium. Secondary-butyllithium is a highly preferred organolithium initiator. Very finely divided lithium having an average particle diameter of less than 2 microns can also be employed as the initiator for the synthesis of living rubbery polymers that can be functionalized with a terminator of formula I in accordance with this invention. U.S. Pat. No. 4,048,420, which is incorporated herein by reference in its entirety, describes the synthesis of lithium terminated living polymers utilizing finely divided lithium as the initiator. Lithium amides can also be used as the initiator in the synthesis of living polydiene rubbers (see U.S. Pat. No. 4,935,471 the teaching of which are incorporated herein by reference with respect to lithium amides that can be used as initiators in the synthesis of living rubbery polymer).

The amount of organolithium initiator utilized will vary depending upon the molecular weight which is desired for the rubbery polymer being synthesized as well as the precise polymerization temperature which will be employed. The precise amount of organolithium compound required to produce a polymer of a desired molecular weight can be easily ascertained by persons skilled in the art. However, as a general rule from 0.01 to 1 phm (parts per 100 parts by weight of monomer) of an organolithium initiator will be utilized. In most cases, from 0.01 to 0.1 phm of an organolithium initiator will be utilized with it being preferred to utilize 0.025 to 0.07 phm of the organolithium initiator.

Many types of unsaturated monomers which contain carbon-carbon double bonds can be polymerized into polymers using such metal catalysts. Elastomeric or rubbery polymers can be synthesized by polymerizing diene monomers utilizing this type of metal initiator system. The diene monomers that can be polymerized into synthetic rubbery polymers can be either conjugated or nonconjugated diolefins. Conjugated diolefin monomers containing from 4 to 8 carbon atoms are generally preferred. Vinyl-substituted aromatic monomers can also be copolymerized with one or more diene monomers into rubbery polymers, for example styrene-butadiene rubber (SBR). Some representative examples of conjugated diene monomers that can be polymerized into rubbery polymers include 1,3-butadiene, isoprene, 1,3-pentadiene, 2,3-dimethyl-1,3-butadiene, 2-methyl-1,3-pentadiene, 2,3-dimethyl-1,3-pentadiene, 2-phenyl-1,3-butadiene, and 4,5-diethyl-1,3-octadiene. Some representative examples of vinyl-substituted aromatic monomers that can be utilized in the synthesis of rubbery polymers include styrene, 1-vinylnapthalene, 3-methylstyrene, 3,5-diethylstyrene, 4-propylstyrene, 2,4,6-trimethylstyrene, 4-dodecylstyrene, 3-methyl-5-normal-hexylstyrene, 4-phenylstyrene, 2-ethyl-4-benzylstyrene, 3,5-diphenylstyrene, 2,3,4,5-tetraethylstyrene, 3-ethyl-1-vinylnapthalene, 6-isopropyl-1-vinylnapthalene, 6-cyclohexyl-1-vinylnapthalene, 7-dodecyl-2-vinylnapthalene, $\alpha$-methylstyrene, and the like.

The metal terminated rubbery polymers that are functionalized with a terminator of formula I in accordance with this invention are generally prepared by solution polymerizations that utilize inert organic solvents, such as saturated aliphatic hydrocarbons, aromatic hydrocarbons, or ethers. The solvents used in such solution polymerizations will normally contain from about 4 to about 10 carbon atoms per molecule and will be liquids under the conditions of the polymerization. Some representative examples of suitable organic solvents include pentane, isooctane, cyclohexane, normal-hexane, benzene, toluene, xylene, ethylbenzene, tetrahydrofuran, and the like, alone or in admixture. For instance, the solvent can be a mixture of different hexane isomers. Such solution polymerizations result in the formation of a polymer cement (a highly viscous solution of the polymer).

The metal terminated living rubbery polymers utilized in the practice of this invention can be of virtually any molecular weight. However, the number average molecular weight of the living rubbery polymer will typically be within the range of about 50,000 to about 500,000. It is more typical for such living rubbery polymers to have number average molecular weights within the range of 100,000 to 250,000.

The metal terminated living rubbery polymer can be functionalized by simply adding a stoichiometric amount of a terminator of formula I to a solution of the rubbery polymer (a rubber cement of the living polymer). In other words, approximately one mole of the terminator of formula I is added per mole of terminal metal groups in the living rubbery polymer. The number of moles of metal end groups in such polymers is assumed to be the number of moles of the metal utilized in the initiator. It is, of course, possible to add greater than a stoichiometric amount of the terminator of formula I. However, the utilization of greater amounts is not beneficial to final polymer properties. Nevertheless, in many cases it will be desirable to utilize a slight excess of the terminator of formula I to insure that at least a stoichiometric amount is actually employed or to control the stoichiometry of the functionalization reaction. In most cases from about 0.8 to about 1.1 moles of the terminator of formula I will be utilized per mole of metal end groups in the living polymer being treated. In the event that it is not desired to functionalize all of the metal terminated chain ends in a rubbery polymer then, of course, lesser amounts of the terminator of formula I can be utilized.

The terminator of formula I will react with the metal terminated living rubbery polymer over a very wide temperature range. For practical reasons the functionalization of such living rubbery polymers will normally be carried out at a temperature within the range of 0° C. to 150° C. In order to increase reaction rates, in most cases it will be preferred to utilize a temperature within the range of 20° C. to 100° C. with temperatures within the range of 50° C. to 80° C. being most preferred. The capping reaction is very rapid and only very short reaction times within the range of 0.5 to 4 hours are normally required. However, in some cases reaction times of up to about 24 hours may be employed to insure maximum conversions.

After the functionalization reaction is completed, it will normally be desirable to "kill" any living polydiene chains which remain. This can be accomplished by adding an alcohol, such as methanol or ethanol, to the polymer cement after the functionalization reaction is completed in order to eliminate any living polymer that was not consumed by the reaction with the terminator of formula I. The end-group functionalized polydiene rubber can then be recovered from the solution utilizing standard techniques.

The functionalized polymer may be compounded into a rubber composition.

The rubber composition may optionally include, in addition to the functionalized polymer, one or more rubbers or elastomers containing olefinic unsaturation. The phrases "rubber or elastomer containing olefinic unsaturation" or "diene based elastomer" are intended to include both natural rubber and its various raw and reclaim forms as well as various synthetic rubbers. In the description of this invention, the terms "rubber" and "elastomer" may be used interchangeably, unless otherwise prescribed. The terms "rubber composition," "compounded rubber" and "rubber compound" are used interchangeably to refer to rubber which has been blended or mixed with various ingredients and materials and such terms are well known to those having skill in the rubber mixing or rubber compounding art. Representative synthetic polymers are the homopolymerization products of butadiene and its homologues and derivatives, for example, methylbutadiene, dimethylbutadiene and pentadiene as well as copolymers such as those formed from butadiene or its homologues or derivatives with other unsaturated monomers. Among the latter are acetylenes, for example, vinyl acetylene; olefins, for example, isobutylene, which copolymerizes with isoprene to form butyl rubber; vinyl compounds, for example, acrylic acid, acrylonitrile (which polymerize with butadiene to form NBR), methacrylic acid and styrene, the latter compound polymerizing with butadiene to form SBR, as well as vinyl esters and various unsaturated aldehydes, ketones and ethers, e.g., acrolein, methyl isopropenyl ketone and vinylethyl ether. Specific examples of synthetic rubbers include neoprene (polychloroprene), polybutadiene (including cis-1,4-polybutadiene), polyisoprene (including cis-1,4-polyisoprene), butyl rubber, halobutyl rubber such as chlorobutyl rubber or bromobutyl rubber, styrene/isoprene/butadiene rubber, copolymers of 1,3-butadiene or isoprene with monomers such as styrene, acrylonitrile and methyl methacrylate, as well as ethylene/propylene terpolymers, also known as ethylene/propylene/diene monomer (EPDM), and in particular, ethylene/propylene/dicyclopentadiene terpolymers. Additional examples of rubbers which may be used include alkoxy-silyl end functionalized solution polymerized polymers (SBR, PBR, IBR and SIBR), silicon-coupled and tin-coupled star-branched polymers. The preferred rubber or elastomers are polyisoprene (natural or synthetic), polybutadiene and SBR.

In one aspect the at least one additional rubber is preferably of at least two of diene based rubbers. For example, a combination of two or more rubbers is preferred such as cis 1,4-polyisoprene rubber (natural or synthetic, although natural is preferred), 3,4-polyisoprene rubber, styrene/isoprene/butadiene rubber, emulsion and solution polymerization derived styrene/butadiene rubbers, c is 1,4-polybutadiene rubbers and emulsion polymerization prepared butadiene/acrylonitrile copolymers.

In one aspect of this invention, an emulsion polymerization derived styrene/butadiene (E-SBR) might be used having a relatively conventional styrene content of about 20 to about 28 percent bound styrene or, for some applications, an E-SBR having a medium to relatively high bound styrene content, namely, a bound styrene content of about 30 to about 45 percent.

By emulsion polymerization prepared E-SBR, it is meant that styrene and 1,3-butadiene are copolymerized as an aqueous emulsion. Such are well known to those skilled in such art. The bound styrene content can vary, for example, from about 5 to about 50 percent. In one aspect, the E-SBR may also contain acrylonitrile to form a terpolymer rubber, as E-SBAR, in amounts, for example, of about 2 to about 30 weight percent bound acrylonitrile in the terpolymer.

Emulsion polymerization prepared styrene/butadiene/acrylonitrile copolymer rubbers containing about 2 to about 40 weight percent bound acrylonitrile in the copolymer are also contemplated as diene based rubbers for use in this invention.

The solution polymerization prepared SBR (S-SBR) typically has a bound styrene content in a range of about 5 to about 50, preferably about 9 to about 36, percent. The S-SBR can be conveniently prepared, for example, by organo lithium catalyzation in the presence of an organic hydrocarbon solvent.

In one embodiment, c is 1,4-polybutadiene rubber (BR) may be used. Such BR can be prepared, for example, by organic solution polymerization of 1,3-butadiene. The BR may be conveniently characterized, for example, by having at least a 90 percent cis 1,4-content.

The cis 1,4-polyisoprene and cis 1,4-polyisoprene natural rubber are well known to those having skill in the rubber art.

The term "phr" as used herein, and according to conventional practice, refers to "parts by weight of a respective material per 100 parts by weight of rubber, or elastomer."

The rubber composition may also include up to 70 phr of processing oil. Processing oil may be included in the rubber composition as extending oil typically used to extend elastomers. Processing oil may also be included in the rubber composition by addition of the oil directly during rubber compounding. The processing oil used may include both extending oil present in the elastomers, and process oil added during compounding. Suitable process oils include various oils as are known in the art, including aromatic, paraffinic, naphthenic, vegetable oils, and low PCA oils, such as MES, TDAE, SRAE and heavy naphthenic oils. Suitable low PCA oils include those having a polycyclic aromatic content of less than 3 percent by weight as determined by the IP346 method. Procedures for the IP346 method may be found in *Standard Methods for Analysis & Testing of Petroleum and Related Products* and *British Standard* 2000 Parts, 2003, 62nd edition, published by the Institute of Petroleum, United Kingdom.

The rubber composition may include from about 10 to about 150 phr of silica. In another embodiment, from 20 to 80 phr of silica may be used.

The commonly employed siliceous pigments which may be used in the rubber compound include conventional pyrogenic and precipitated siliceous pigments (silica). In one embodiment, precipitated silica is used. The conventional siliceous pigments employed in this invention are precipitated silicas such as, for example, those obtained by the acidification of a soluble silicate, e.g., sodium silicate.

Such conventional silicas might be characterized, for example, by having a BET surface area, as measured using nitrogen gas. In one embodiment, the BET surface area may be in the range of about 40 to about 600 square meters per gram. In another embodiment, the BET surface area may be in a range of about 80 to about 300 square meters per gram. The BET method of measuring surface area is described in the *Journal of the American Chemical Society*, Volume 60, Page 304 (1930).

The conventional silica may also be characterized by having a dibutylphthalate (DBP) absorption value in a range of about 100 to about 400, alternatively about 150 to about 300.

The conventional silica might be expected to have an average ultimate particle size, for example, in the range of 0.01 to 0.05 micron as determined by the electron microscope, although the silica particles may be even smaller, or possibly larger, in size.

Various commercially available silicas may be used, such as, only for example herein, and without limitation, silicas commercially available from PPG Industries under the Hi-Sil trademark with designations 210, 243, etc; silicas available from Rhodia, with, for example, designations of Z1165MP and Z165GR and silicas available from Degussa AG with, for example, designations VN2 and VN3, etc.

Commonly employed carbon blacks can be used as a conventional filler in an amount ranging from 10 to 150 phr. In another embodiment, from 20 to 80 phr of carbon black may be used. Representative examples of such carbon blacks include N110, N121, N134, N220, N231, N234, N242, N293, N299, N315, N326, N330, N332, N339, N343, N347, N351, N358, N375, N539, N550, N582, N630, N642, N650, N683, N754, N762, N765, N774, N787, N907, N908, N990 and N991. These carbon blacks have iodine absorptions ranging from 9 to 145 g/kg and DBP number ranging from 34 to 150 cm$^3$/100 g.

Other fillers may be used in the rubber composition including, but not limited to, particulate fillers including ultra high molecular weight polyethylene (UHMWPE), crosslinked particulate polymer gels including but not limited to those disclosed in U.S. Pat. Nos. 6,242,534; 6,207,757; 6,133,364; 6,372,857; 5,395,891; or 6,127,488, and plasticized starch composite filler including but not limited to that disclosed in U.S. Pat. No. 5,672,639. Such other fillers may be used in an amount ranging from 1 to 30 phr.

In one embodiment the rubber composition may contain a conventional sulfur containing organosilicon compound. In one embodiment, the sulfur containing organosilicon compounds are the 3,3'-bis(trimethoxy or triethoxy silylpropyl) polysulfides. In one embodiment, the sulfur containing organosilicon compounds are 3,3'-bis(triethoxysilylpropyl) disulfide and/or 3,3'-bis(triethoxysilylpropyl)tetrasulfide.

In another embodiment, suitable sulfur containing organosilicon compounds include compounds disclosed in U.S. Pat. No. 6,608,125. In one embodiment, the sulfur containing organosilicon compounds includes 3-(octanoylthio)-1-propyltriethoxysilane, $CH_3(CH_2)_6C(\!\!=\!\!O)\!\!-\!\!S\!\!-\!\!CH_2CH_2CH_2Si(OCH_2CH_3)_3$, which is available commercially as NXT™ from Momentive Performance Materials.

In another embodiment, suitable sulfur containing organosilicon compounds include those disclosed in U.S. Patent Publication No. 2003/0130535. In one embodiment, the sulfur containing organosilicon compound is Si-363 from Degussa.

The amount of the sulfur containing organosilicon compound in a rubber composition will vary depending on the level of other additives that are used. Generally speaking, the amount of the compound will range from 0.5 to 20 phr. In one embodiment, the amount will range from 1 to 10 phr.

It is readily understood by those having skill in the art that the rubber composition would be compounded by methods generally known in the rubber compounding art, such as mixing the various sulfur-vulcanizable constituent rubbers with various commonly used additive materials such as, for example, sulfur donors, curing aids, such as activators and retarders and processing additives, such as oils, resins including tackifying resins and plasticizers, fillers, pigments, fatty acid, zinc oxide, waxes, antioxidants and antiozonants and peptizing agents. As known to those skilled in the art, depending on the intended use of the sulfur vulcanizable and sulfur-vulcanized material (rubbers), the additives mentioned above are selected and commonly used in conventional amounts. Representative examples of sulfur donors include elemental sulfur (free sulfur), an amine disulfide, polymeric polysulfide and sulfur olefin adducts. In one embodiment, the sulfur-vulcanizing agent is elemental sulfur. The sulfur-vulcanizing agent may be used in an amount ranging from 0.5 to 8 phr, alternatively with a range of from 1.5 to 6 phr. Typical amounts of tackifier resins, if used, comprise about 0.5 to about 10 phr, usually about 1 to about 5 phr. Typical amounts of processing aids comprise about 1 to about 50 phr. Typical amounts of antioxidants comprise about 1 to about 5 phr. Representative antioxidants may be, for example, diphenyl-p-phenylenediamine and others, such as, for example, those disclosed in The Vanderbilt Rubber Handbook (1978), Pages 344 through 346. Typical amounts of antiozonants comprise about 1 to 5 phr. Typical amounts of fatty acids, if used, which can include stearic acid comprise about 0.5 to about 3 phr. Typical amounts of zinc oxide comprise about 2 to about 5 phr. Typical amounts of waxes comprise about 1 to about 5 phr. Often microcrystalline waxes are used. Typical amounts of peptizers comprise about 0.1 to about 1 phr. Typical peptizers may be, for example, pentachlorothiophenol and dibenzamidodiphenyl disulfide.

Accelerators are used to control the time and/or temperature required for vulcanization and to improve the properties of the vulcanizate. In one embodiment, a single accelerator system may be used, i.e., primary accelerator. The primary accelerator(s) may be used in total amounts ranging from about 0.5 to about 4, alternatively about 0.8 to about 1.5, phr. In another embodiment, combinations of a primary and a secondary accelerator might be used with the secondary accelerator being used in smaller amounts, such as from about 0.05 to about 3 phr, in order to activate and to improve the properties of the vulcanizate. Combinations of these accelerators might be expected to produce a synergistic effect on the final properties and are somewhat better than those produced by use of either accelerator alone. In addition, delayed action accelerators may be used which are not affected by normal processing temperatures but produce a satisfactory cure at ordinary vulcanization temperatures. Vulcanization retarders might also be used. Suitable types of accelerators that may be used in the present invention are amines, disulfides, guanidines, thioureas, thiazoles, thiurams, sulfenamides, dithiocarbamates and xanthates. In one embodiment, the primary accelerator is a sulfenamide. If a second accelerator is used, the secondary accelerator may be a guanidine, dithiocarbamate or thiuram compound.

The mixing of the rubber composition can be accomplished by methods known to those having skill in the rubber mixing art. For example, the ingredients are typically mixed in at least two stages, namely, at least one non-productive stage followed by a productive mix stage. The final curatives including sulfur-vulcanizing agents are typically mixed in the final stage which is conventionally called the "productive" mix stage in which the mixing typically occurs at a temperature, or ultimate temperature, lower than the mix temperature(s) than the preceding non-productive mix stage(s). The terms "non-productive" and "productive" mix stages are well known to those having skill in the rubber mixing art. The rubber composition may be subjected to a thermomechanical mixing step. The thermomechanical mixing step generally comprises a mechanical working in a mixer or extruder for a period of time suitable in order to produce a rubber temperature between 140° C. and 190° C. The appropriate duration of the thermomechanical working varies as a function of the operating conditions, and the volume and nature of the components. For example, the thermomechanical working may be from 1 to 20 minutes.

The rubber composition may be incorporated in a variety of rubber components of the tire. For example, the rubber component may be a tread (including tread cap and tread base), sidewall, apex, chafer, sidewall insert, wirecoat or innerliner. In one embodiment, the component is a tread.

The pneumatic tire of the present invention may be a race tire, passenger tire, aircraft tire, agricultural, earthmover, off-the-road, truck tire, and the like. In one embodiment, the tire is a passenger or truck tire. The tire may also be a radial or bias.

Vulcanization of the pneumatic tire of the present invention is generally carried out at conventional temperatures ranging from about 100° C. to 200° C. In one embodiment, the vulcanization is conducted at temperatures ranging from about 110° C. to 180° C. Any of the usual vulcanization processes may be used such as heating in a press or mold, heating with superheated steam or hot air. Such tires can be built, shaped, molded and cured by various methods which are known and will be readily apparent to those having skill in such art.

This invention is illustrated by the following examples that are merely for the purpose of illustration and are not to be regarded as limiting the scope of the invention or the manner in which it can be practiced. Unless specifically indicated otherwise, parts and percentages are given by weight.

Example 1

Synthesis of propaneamide, N,N-dimethyl-3-[[3-(triethoxysilyl)propyl]thio]-

Synthesis of siloxy functionalized acrylamide is based on thiol-ene reaction mechanism in which thiol is 3-mercaptopropyltriethoxysilane and ene is N,N-dimethylacrylamide. Triethylamine was used as catalyst which initiates the formation of enolate in synthesis of the siloxy functionalized acrylamide.

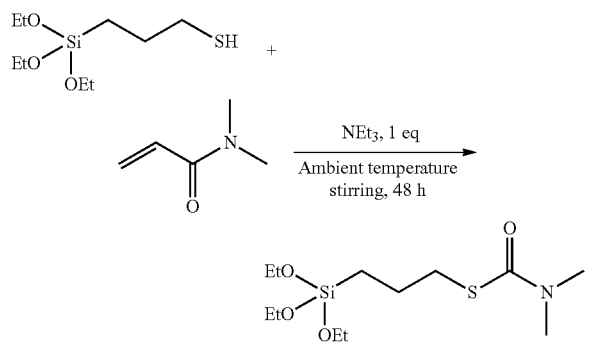

To a stirred solution of 3-(mercaptopropyl)triethoxysilane (30 mmol) in 50 mL of anhydrous ethanol was added N,N-dimethylacrylamide (30 mmol) at ambient temperature. To the solution of reactants was added triethylamine (30 mmol) and resulting solution was stirred at ambient temperature for 48 h. The mixture was concentrated under reduced pressure and dried overnight in Schlenk line. The product was obtained in 90% yield. The synthesized compound was characterized via $^1$H-NMR (400 MHz) and HPLC (88.4% purity). The chemical structures were characterized via NMR (400 MHz) as shown in FIG. 1.

Example 2

Synthesis of 2,5-pyrrolidinedione, 1-methyl-3-[[3-(triethoxysilyl)propyl]thio]-

Synthesis of siloxy functionalized maleimide is based on thiol-ene reaction mechanism in which thiol is 3-mercaptopropyltriethoxysilane and ene is N-methylmaleimide. Triethylamine was used as catalyst which initiates the formation of enolate in synthesis of siloxy functionalized maleimide.

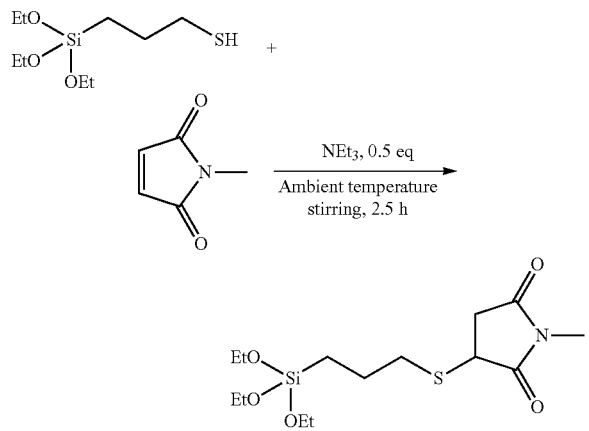

Figure 2:
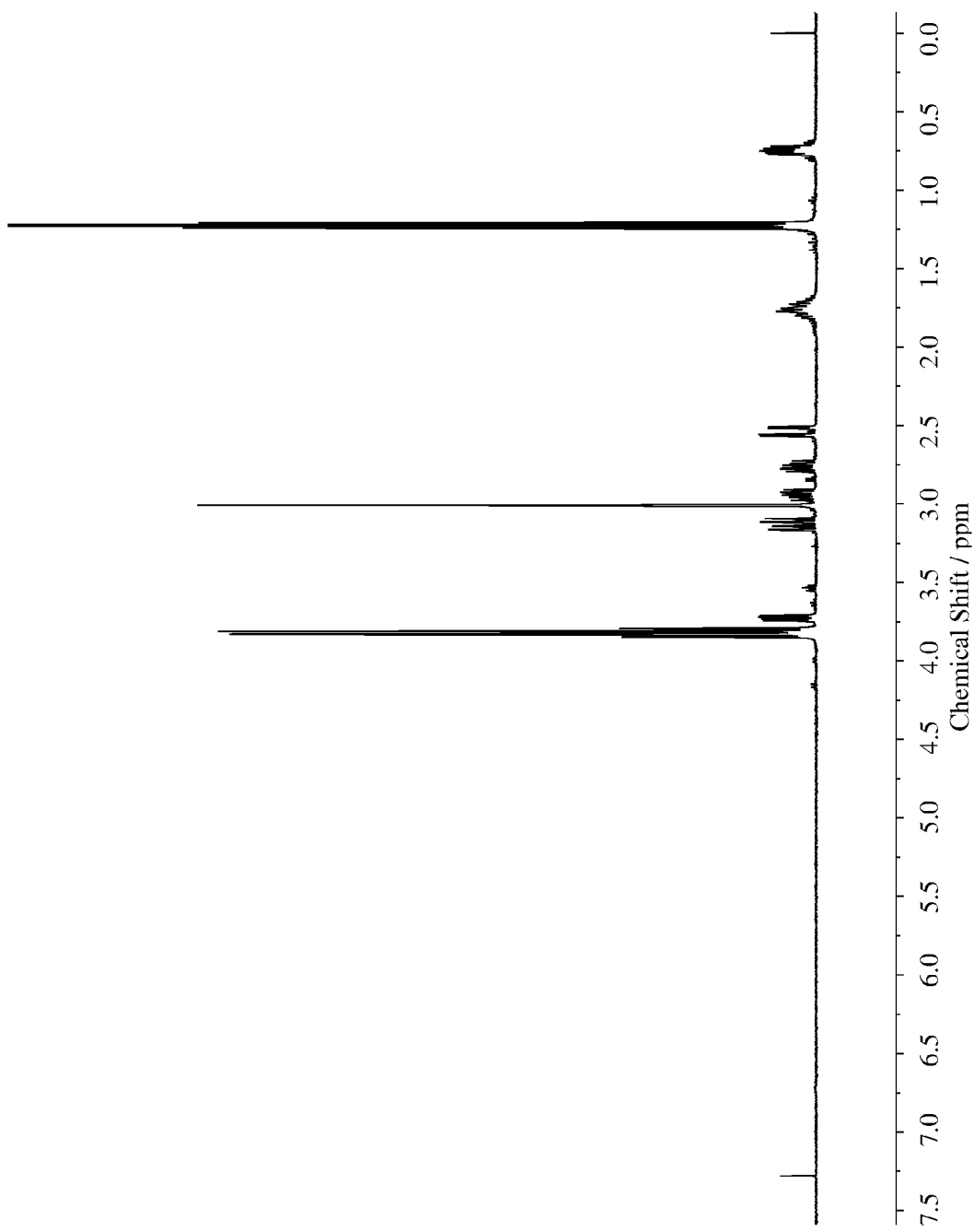
FIG. 2 shows the $^1$H NMR of 2,5-pyrrolidinedione, 1-methyl-3-[[3-(triethoxysilyl)propyl]thiol]-.

To 250 mL round bottomed flask, maleimide (30 mmol) and 50 mL ethanol was added. To this solution 3-(mercaptopropyltriethoxysilane) (30 mmol) and triethylamine (15 mmol) was added and mixture was stirred for 2.5 h at ambient temperature. The mixture was concentrated under reduced pressure and dried overnight in Schlenk line. The product was obtained in 91% yield. The synthesized compound was characterized via $^1$H-NMR (400 MHz) and HPLC (95.8% purity)/ The chemical structures were characterized via NMR (400 MHz) as shown in FIG. 2.

Example 3

Co-Polymerization of Styrene and Butadiene

Polymerizations were done in a 1 gallon reactor at 65° C. Monomer premix of styrene and butadiene was charged into reactor with hexane as solvent followed by addition of modifier (TMEDA) and initiator (n-butyllithium). When the conversion was above 98%, the polymerizations were terminated with isopropanol or with functional terminator propanamide, N,N-dimethyl-3-[[3-(triethoxysilyl)propyl]thio]- from Example 1, or 2,5-pyrrolidinedione, 1-methyl-3-[[3-(triethoxysilyl)propyl]thio]- from Example 2.

The polymers obtained were characterized using different techniques, for example, size exclusion chromotography (SEC) for determination of molecular weight, dynamic scanning calorimetry (DSC) for determination of Tg, IR for determining cis, trans, styrene and vinyl content, and Mooney viscosity measurements with results given in Tables 1 and 2.

TABLE 1

| Polymer Sample | Overall Mn (g/mol) | PDI |
|---|---|---|
| 1: Sulfanylsilane-SBR[1] (Comparative) | 250,000 | 1.42 |
| 2: SBR[2] (Control) | 182,000 | 1.02 |
| 3: Acrylamide-SBR[3] | 248,000 | 1.41 |
| 4: Maleimide-SBR[4] | 218,000 | 1.17 |

[1]Sulfanylsilane functionalized solution polymerized styrene-butadiene rubber, available commercially as Sprintan ® SLR 4602, from Styron.
[2]Solution polymerized styrene-butadiene rubber terminated using isopropanol, from The Goodyear Tire & Rubber Company.
[3]Solution polymerized styrene-butadiene terminated with propanamide, N,N-dimethyl-3-[[3-(triethoxysilyl)propyl]thio]-.
[4]Solution polymerized styrene-butadiene terminated with 2,5-pyrrolidinedione, 1-methyl-3-[[3-(triethoxysilyl)propyl]thio]-.

TABLE 2

| Polymer Sample | Mooney | Cis | Trans | Styrene | Vinyl[1] | Tg (° C.) |
|---|---|---|---|---|---|---|
| 1: Sulfanylsilane-SBR (Comparative) | 65 | 12.15 | 21.88 | 17.97 | 48 | −25.0 |
| 2: Non-functionalized-SBR (Control) | 35.9 | 13.07 | 18.29 | 23.70 | 44.94 | −22.1 |
| 3: Acrylamide-SBR | 46.3 | 11.88 | 21.99 | 26.90 | 39.33 | −22.2 |
| 4: Maleimide-SBR | 57.9 | 13.02 | 18.39 | 25.06 | 43.52 | −22.0 |

[1]Vinyl content expressed as weight percent based on total polymer weight.

Example 4

Mixing Studies and Compound Testing

Each of the functionalized SBR copolymers of Example 3 (functionalized using siloxy acrylamide {propanamide, N,N-dimethyl-3-[[3-(triethoxysilyl)propyl]thio]-} and siloxy maleimide {2,5-pyrrolidinedione, 1-methyl-3-[[3-(triethoxysilyl)propyl]thio]-} as well as control and a comparative sulfanylsilane functionalized SBR were used to make rubber compounds.

Rubber compounds were mixed in a 3-piece 75 mL CW Brabender® mixer equipped with Banbury® rotor. Each SBR sample was mixed with additives in a three stage mix procedure as shown in Table 3, with all amounts given in parts by weight, per 100 parts by weight of elastomer (phr). In the first non-productive mix stage, compounds were mixed for 4 minutes at 60 rpm using 140° C. as starting temperature. All compounds were pressed in a compression molding machine for 1 minute before a second non-productive mix stage. In the second non productive step mixing conditions were the same as in the first non-productive step, with mix time of 3 minutes. Productive mixes were carried out using 60° C. starting temperature and 60 rpm with mix time of 3 minute.

TABLE 3

| Variable (Addition as indicated in Examples 5-8) | |
|---|---|
| Silane[1] | 5.2 |
| First Non Productive Step | |
| SBR | 100 |
| Silica | 65 |
| Process Oil | 30 |
| Stearic Acid | 2 |
| Zinc Oxide | 3.5 |
| Second Non Productive Step | |
| Remixing | |
| Productive Mix Step | |
| Sulfur | 1.7 |
| Accelerators[2] | 3.1 |
| Antidegradant | 0.75 |

[1]Bis(triethoxysilylpropyl) disulfide
[2]Sulfenamide and guanidine types

The compounds were tested for silica interaction using an RPA 2000® from Alpha Technology. Non-productive compounds were first heated to 160° C. and the torque increase was monitored as a function of time using 1 Hz and 0.48% strain in order to determine the rate of the filler "flocculation". Subsequently the compounds were cooled to 40° C. and a strain sweep was carried out using 1 Hz in order to determine the Payne effect, i.e., the strain dependence of G', G" and tan delta. Cure was carried out at 160° C. using 7% strain. Cured compounds dynamic properties were measured first by curing the sample at 160° C. for 30 minute at the lowest possible strain to mimic a static cure. After this samples were cooled and tested in the given manner for green compounds.

Example 5

Samples 5-8: Nonproductive Compound with Added Silane Coupling Agent

Figure 3:
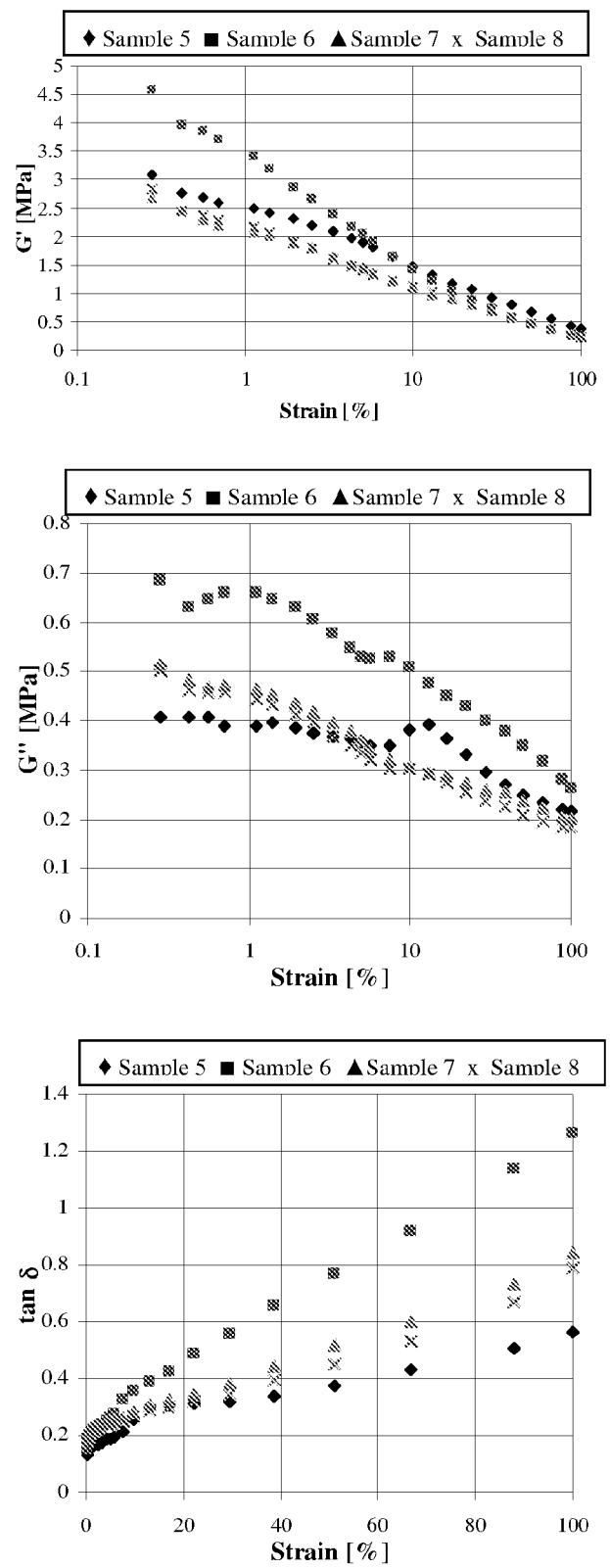
FIG. 3 shows graphs of G', G" and tan delta versus strain for non-productive samples with silane coupling agent.

FIG. 3 shows the results of the strain sweeps conducted at 40° C. on the non-productive compounds with silane coupling agent after 30 minutes heat treatment of the samples at low strain at 160° C. in the RPA. As shown in FIG. 3, G' and tan delta of non-functionalized control sample 6 shows highest strain dependency. The comparative sulfanylsilane functionalized polymer (sample 5), siloxy acrylamide (sample 7) and siloxy maleimide (sample 8) functionalized polymer shows reduced strain dependency which indicates less filler-filler interaction or more filler polymer interaction.

The ratio of the low amplitude (0.48% strain) modulus (LAM) and high amplitude (100% strain) modulus (HAM) is a measure of the Payne effect and is given in Table 4 for the various samples. Higher the LAM/HAM ratio less is polymer-filler interaction. As shown in Table 4, non-functionalized control polymer sample shows highest LAM/HAM value indicating least polymer-filler interaction while sulfanylsilane, siloxy acrylamide and siloxy maleimide functionalized polymer shows lower LAM/HAM ratio.

TABLE 4

| SBR Sample | LAM/HAM | Tan Delta (40° C.) (5% strain) |
|---|---|---|
| 5 (Sulfanylsilane-SBR) | 7.2 | 0.19 |
| 6 (Control) | 18.9 | 0.26 |
| 7 (Acrylamide-SBR) | 10.3 | 0.25 |
| 8 (Maleimide-SBR) | 10.5 | 0.24 |

Example 6

Samples 9-12: Non-Productive Compound with Added Silane Coupling Agent

Figure 4:
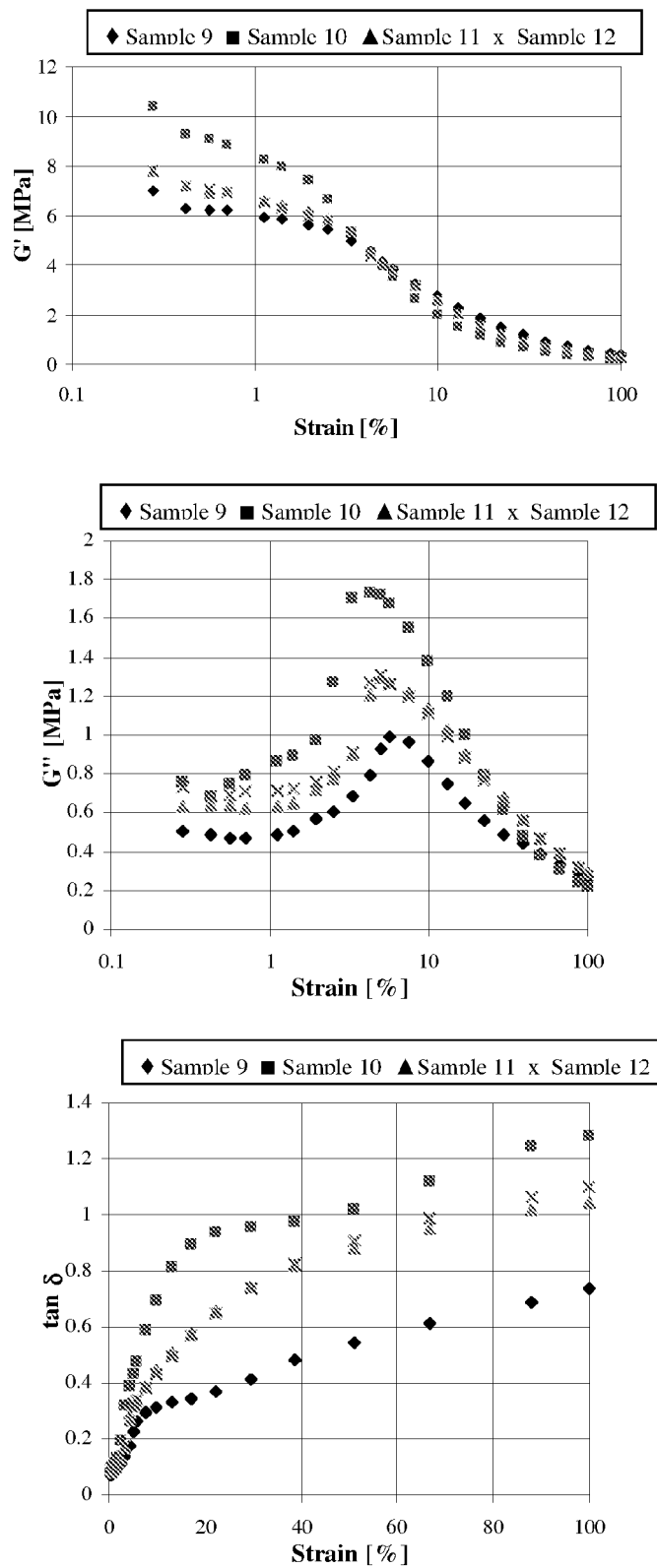
FIG. 4 shows graphs of G', G" and tan delta versus strain for non-productive samples without silane coupling agent.

FIG. 4 shows the results of the strain sweeps conducted at 40° C. on the non-productive compounds without any silane coupling agent after 30 minutes heat treatment of the samples at low strain at 160° C. in the RPA. In this case no coupling agent was added to evaluate solely interaction between polymer chain ends and filler. In this case, similar to results obtained when coupling agent was used, G' and tan delta of control polymer sample shows highest strain dependency. Sulfanylsilane (sample 9), siloxy acrylamide (sample 11) and siloxy maleimide (sample 12) functionalized polymer samples shows reduced strain dependency.

The ratio of the low amplitude (0.48% strain) and high amplitude (100% strain) moduli is shown in Table 5. Without the use of silane coupling agent, Payne effect is enhanced as compared to Payne effect observed with the use of silane coupling agent. The control sample shows highest LAM/HAM value, i.e., relatively high Payne effect. Sulfanylsilane, siloxy acrylamide and siloxy maleimide functionalized polymer shows lower Payne effect indicating good polymer-filler interaction. As the result of good polymer-filler interaction, tan delta values for the sulfanylsilane, siloxy acrylamide and siloxy maleimide functionalized polymers are lower than non-functionalized control.

TABLE 5

| SBR Sample No. | LAM/HAM | Tan Delta (40° C.) (5% strain) |
|---|---|---|
| 9 (Sulfanylsilane-SBR) | 17.5 | 0.22 |
| 10 (Control) | 53.8 | 0.43 |
| 11 (Acrylamide-SBR) | 25.9 | 0.32 |
| 12 (Maleimide-SBR) | 28.0 | 0.33 |

Example 7

Samples 13-16: Productive Compound with Added Silane Coupling Agent

In this example, the addition of silane in productive compound is illustrated. Compound mixing was done with a first non-productive mix stage followed by the second non-productive step and finally productive step. Addition of the silane coupling agent was done in the first non-productive mix stage.

Figure 5:
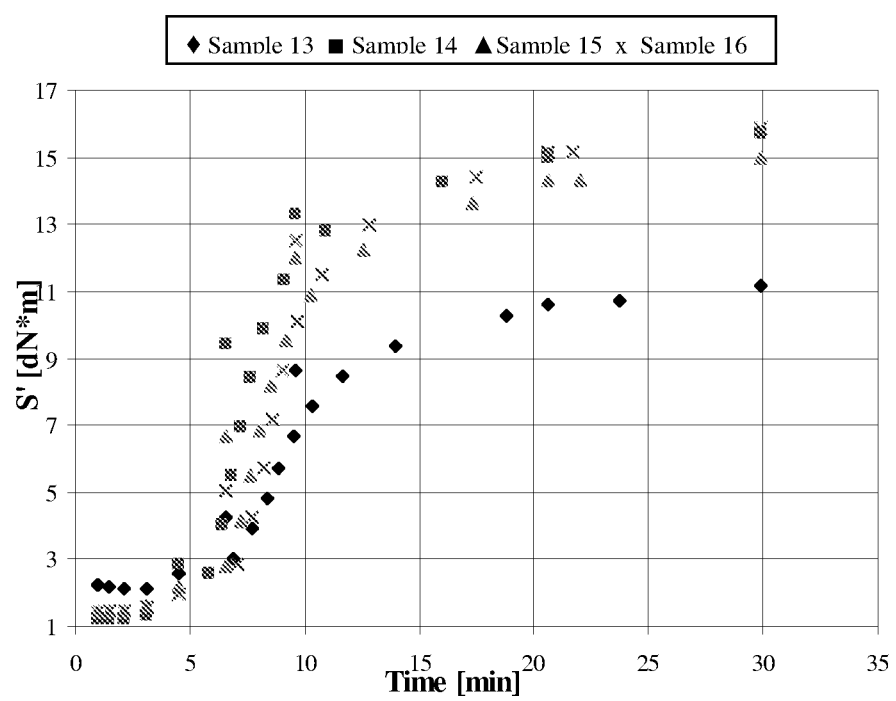
FIG. 5 shows a cure curve obtained at 7% strain for productive batches with silane coupling agent.

The cure curves obtained with silane coupling agent at 7% strain is shown in FIG. 5. Cure parameters max torque S' max and change in torque delta S' are given in Table 6.

TABLE 6

Maximum and delta torque values for productive batches with silane coupling agent

| SBR Sample No. | S'max (dN * m) | Delta S' (dN * m) |
|---|---|---|
| 13 (Sulfanylsilane-SBR) | 11.18 | 9.08 |
| 14 (Control) | 15.7 | 14.56 |
| 15 (Acrylamide-SBR) | 14.27 | 13.05 |
| 16 (Maleimide-SBR) | 15.87 | 14.49 |

Figure 6:
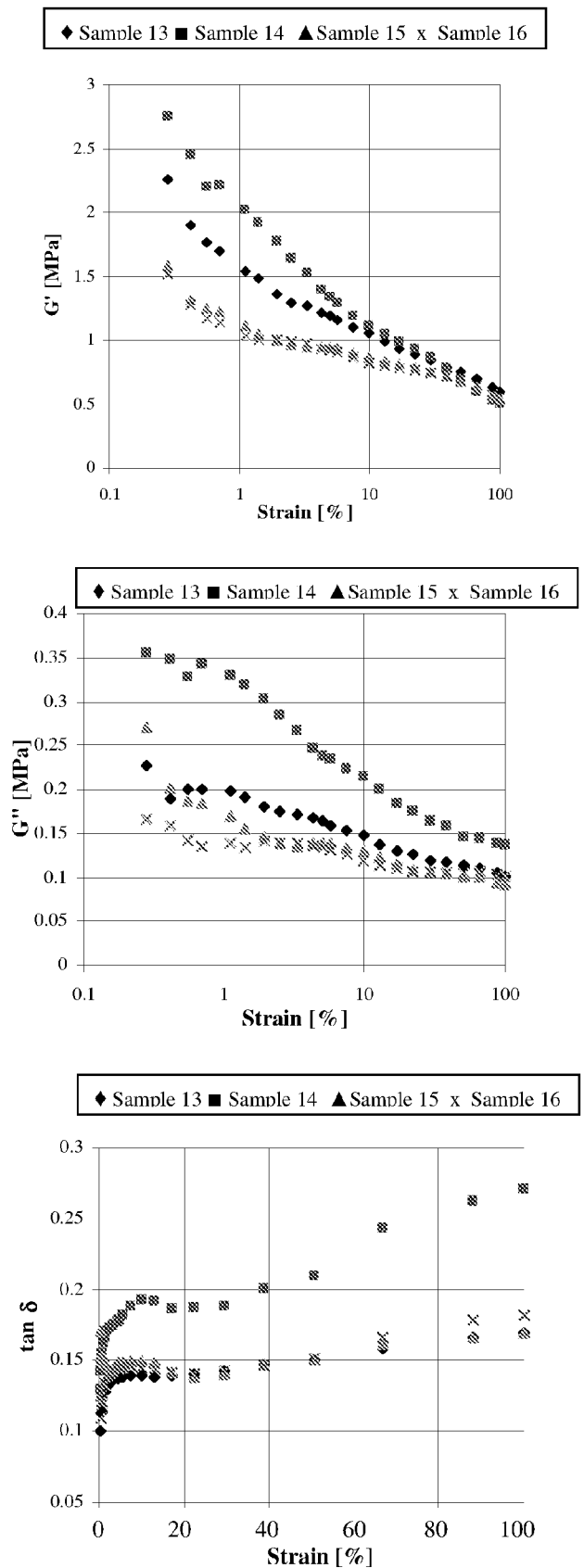
FIG. 6 shows graphs of G', G" and tan delta versus strain for productive samples with silane coupling agent.

The strain sweeps were conducted in separate RPA runs. In these runs the samples were cured at 160° C. for 30 minutes using the lowest possible strain (0.28%) in order to mimic static cure and not to alter filler-filler or filler-polymer interaction. Strain sweep cures were obtained at 40° C. as shown in FIG. 6.

The ratio of the low amplitude (0.48% strain) and high amplitude (100% strain) moduli is shown in Table 7. The strain sweeps conducted on the cured compounds indicates that siloxy acrylamide and siloxy maleimide functionalized polymer samples shows lower Payne effect than the sulfanylsilane functionalized polymer, so improved polymer filler interaction.

TABLE 7

| SBR Sample No. | LAM/HAM | Tan Delta (40° C.) (5% strain) | Tan Delta (30° C.) (10% strain) ARES strain sweep |
|---|---|---|---|
| 1 Sulfanylsilane-SBR | 3.2 | 0.14 | 0.16 |
| 2 Control | 4.8 | 0.18 | 0.18 |
| 3 Acrylamide-SBR | 2.4 | 0.15 | 0.16 |
| 4 Maleimide-SBR | 2.3 | 0.14 | 0.16 |

Example 8

Productive Compounds without Added Silane Coupling Agent

Figure 7:
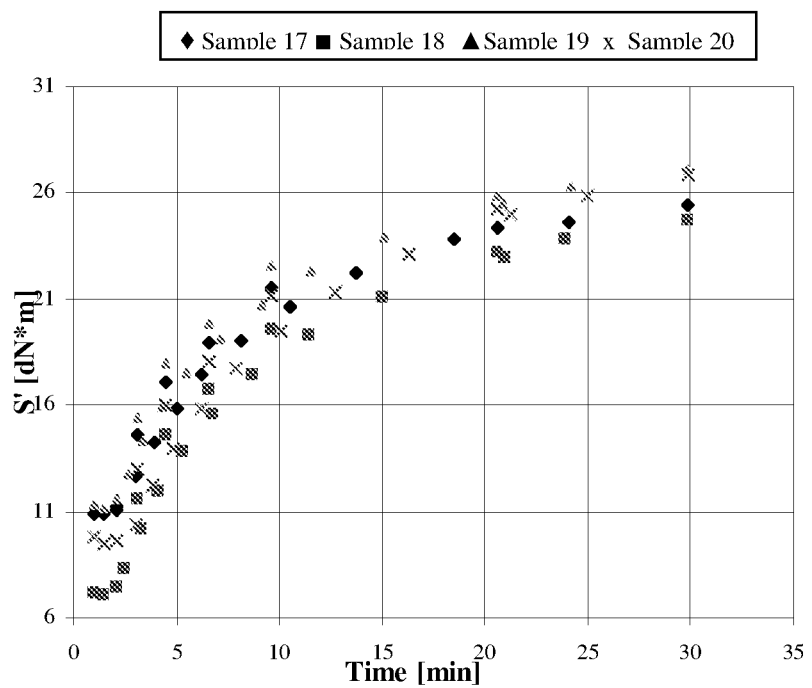
FIG. 7 shows a cure curve obtained at 7% strain for productive batches without silane coupling agent.

In this example, mixing of productive compound without addition of silane coupling agent is illustrated. Compound mixing was done similar to one used for productive batches with silane coupling agent. The cure curve for productive sample without silane coupling agent at 7% strain is shown in FIG. 7. Cure parameters max torque S' max and change in torque delta S' are given in Table 8.

TABLE 8

| SBR Sample No. | S'max (dN * m) | Delta S' (dN * m) |
|---|---|---|
| 1 Sulfanylsilane-SBR | 25.42 | 15.99 |
| 2 Control | 24.72 | 18.21 |
| 3 Acrylamide-SBR | 27.14 | 16.04 |
| 4 Maleimide-SBR | 26.79 | 18.24 |

Figure 8:
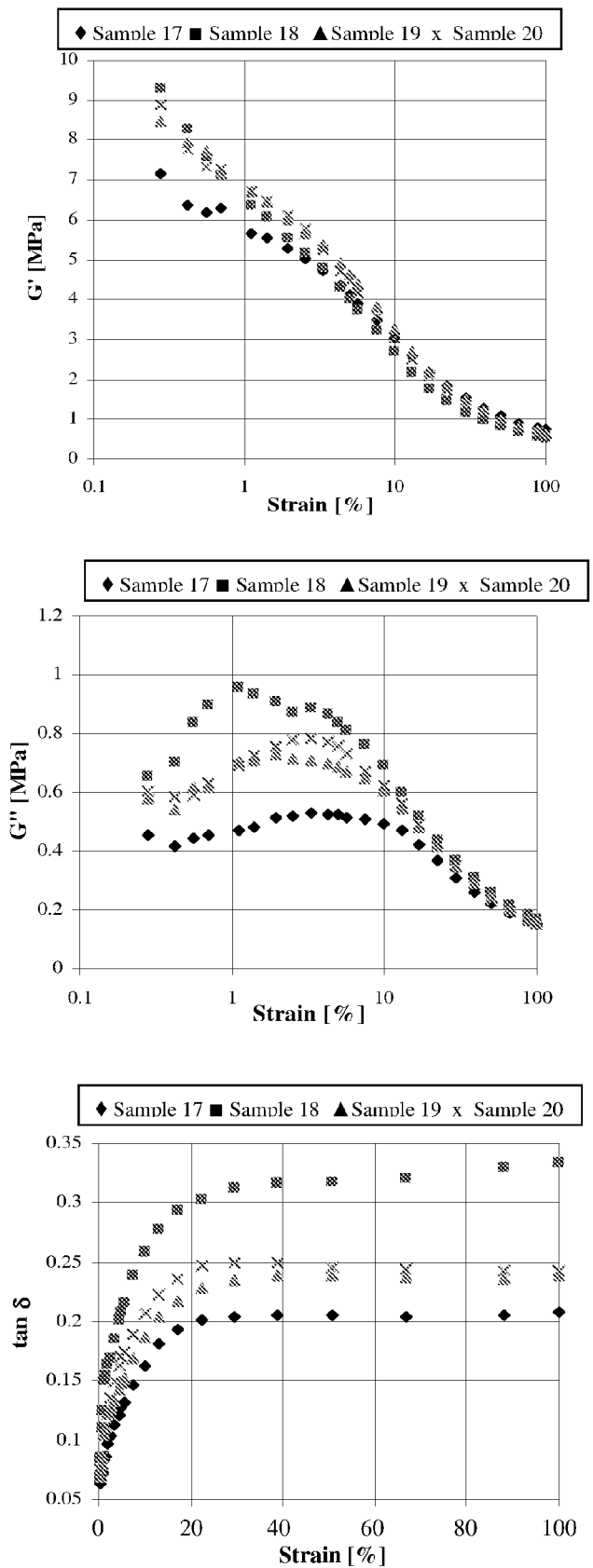
FIG. 8 shows graphs of G', G" and tan delta versus strain for productive samples without silane coupling agent.

The strain sweeps were conducted in separate RPA runs. In these runs the sample were cured at 160° C. for 30 minutes using the lowest possible strain (0.28%) in order to mimic static cure and not to alter filler-filler or filler-polymer interaction. The ratio of the low amplitude (0.48% strain) and high amplitude (100% strain) moduli is shown in Table 9. Strain sweep curves were obtained at 40° C. as shown in FIG. 8.

TABLE 9

| SBR Sample No. | LAM/HAM | Tan Delta (5% strain) | Tan Delta (30° C.) (10% strain) ARES strain sweep |
|---|---|---|---|
| 1 Sulfanylsilane-SBR | 8.7 | 0.13 | 0.18 |
| 2 Control | 16.2 | 0.21 | 0.18 |
| 3 Acrylamide-SBR | 12.1 | 0.15 | 0.19 |
| 4 Maleimide-SBR | 12.6 | 0.17 | 0.18 |

The strain sweeps conducted on the cured compounds indicates that siloxy acrylamide and siloxy maleimide functionalized polymer shows reduced Payne effect, indicating improved polymer filler interaction compared to non-functionalized polymer control. In addition, tan delta values for sulfanylsilane and siloxy acrylamide and siloxy maleimide functionalized polymers are lower as compared to non-functionalized control sample.

As shown above, both comparative and siloxy acrylamide and siloxy maleimide functionalized polymer samples shows reduced Payne effect as well lower tan delta values as compared to non-functionalized control sample. This can be explained by difference in end groups which are present in these polymers.

In the comparative polymer, it is assumed that the polymer is terminated using end terminating agent based on siloxy and sulfur silane groups as described in patent publication US2008/0287601. Without wishing to be bound by any theory, for the polymer chain carrying both siloxy as well sulfur-silane groups, the siloxy groups help in providing covalent interaction with silica surface and sulfur protected with silane helps in providing interaction between polymer chains. The sulfur-silane group has the potential to cleave off during mixing and therefore results in generation of active thiol groups which can help in achieving cross-linking between polymer chains. In addition, the comparative polymer is likely coupled with an agent such as $SnCl_4$ which can help in achieving better processabilty.

The siloxy acrylamide and siloxy maleimide functionalized polymer samples of the present invention are terminated using end terminating agent based on siloxy and dimethyl acrylamide or methyl maleimide groups. Again, while not wishing to be bound by any theory, it is thought that similar to the comparative polymer, siloxy groups helps in providing covalent interaction with silica and amine groups helps in achieving good interaction between polymer chains and silica. When siloxy functionalized acrylamide or maleimide is used as end terminating agent, there is the possibility of active polymer chain to be attached to terminating agent group via nucleophilic displacement of alkoxy group as well as polymer chain can also be attached at carbonyl bond. Polymer chain attached to siloxy group helps in attaining good interaction between polymer chain and filler. In contrast to the comparative sulfanysilane functionalized polymer, with the use of siloxy acrylamide or siloxy maleimide end terminating agent, it is also possible to achieve coupling between polymer chains without addition of any additional $SnCl_4$ because the end terminating agent based on siloxy acrylamide or maleimide group might interact with living anionic polymer chain in two different ways. One way is substitution of ethoxide group present on siloxy acrylamide or maleimide with polymer chain and second way is reaction of anionic polymer chain with carbonyl group. This theorized mechanism of action of siloxy acrylamide and siloxy maleimide end terminating agent is shown in Scheme 1 and 2. Here, $P^+Li^-$ indicates the living polymer P with the lithium end group Li.

Scheme 1 Theorized mechanism of action of siloxy acrylamide end terminating agent

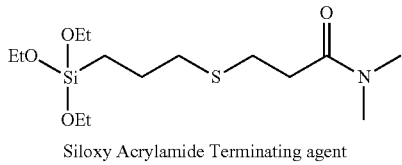

Siloxy Acrylamide Terminating agent

Polymer Functionalization Using Siloxy Acrylamide

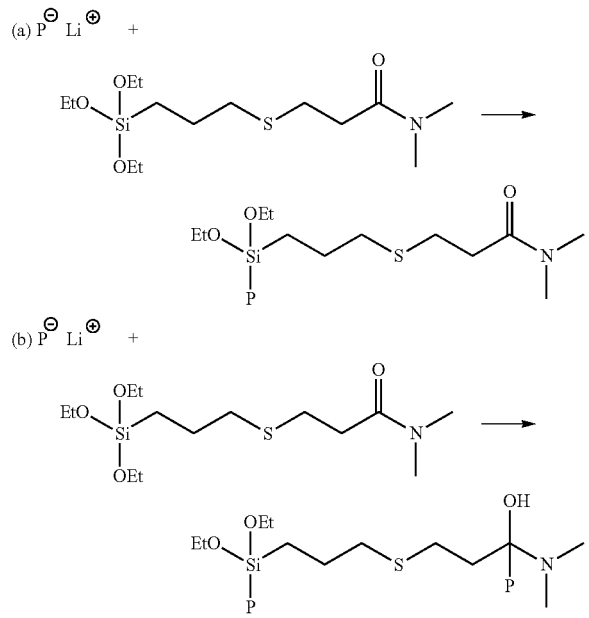

Scheme 2 Theorized mechanism of action of siloxy maleimide end terminating agent

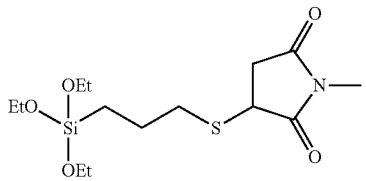

Siloxy Maleimide Terminating agent

Polymer Functionalization Using Siloxy Maleimide

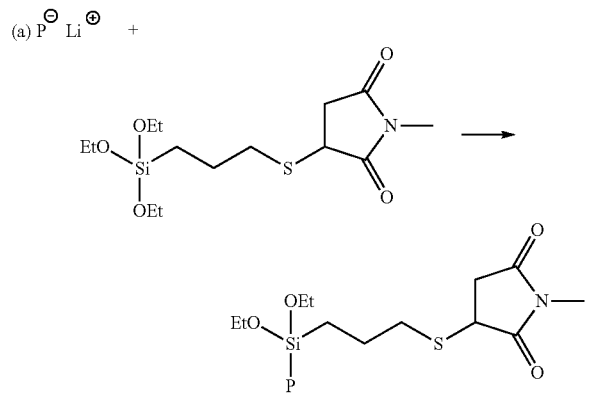

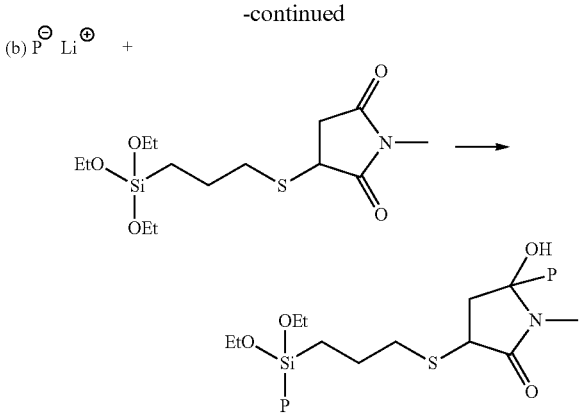

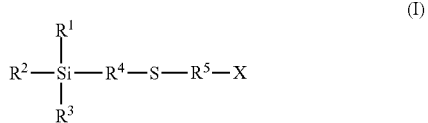

While certain representative embodiments and details have been shown for the purpose of illustrating the subject invention, it will be apparent to those skilled in this art that various changes and modifications can be made therein without departing from the scope of the subject invention.

What is claimed is:

1. A functionalized elastomer comprising the reaction product of a living anionic elastomeric polymer and a polymerization terminator of formula I

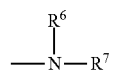

(I)

$$R^2-\underset{\underset{R^3}{|}}{\overset{\overset{R^1}{|}}{Si}}-R^4-S-R^5-X$$

wherein:

$R^1$, $R^2$ and $R^3$ are independently C1 to C8 alkyl or C1 to C8 alkoxy with the proviso that at least two of $R^1$, $R^2$ and $R^3$ are C1 to C8 alkoxy;

$R^4$ is C1 to C8 alkanediyl, C6 to C8 arylene, C7 to C8 alkylarylene, or C7 to C8 arylalkanediyl; Si is silicon; S is sulfur;

X is —O—$R^6$ or $$-\underset{\underset{}{|}}{\overset{\overset{R^6}{|}}{N}}-R^7$$

wherein O is oxygen; N is nitrogen; and i) $R^5$ is —$(CH_2)_2$—C(=O)— wherein the $(CH_2)_2$ group is adjacent to the sulfur and $R^6$ and $R^7$ are independently hydrogen or C1 to C8 alkyl, C6 to C8 aryl, or C7 to C8 arylalkyl; or ii) $R^5$ and $R^6$ taken together with the heteroatom nitrogen or heteroatom oxygen to which both $R^5$ and $R^6$ are attached form a 5 membered ring wherein $R^5$ is —CH—C(=O)— wherein the carbonyl group is adjacent to the heteroatom and $R^6$ is —$CH_2$—C(=O)— wherein the carbonyl group is adjacent to the heteroatom and $R^7$ is hydrogen or C1 to C8 alkyl, C6 to C8 aryl, or C7 to C8 arylalkyl.

2. The functionalized elastomer of claim 1, wherein $R^1$, $R^2$ and $R^3$ are each C1 to C8 alkoxy.

3. The functionalized elastomer of claim 1, wherein the living anionic elastomer is derived from at least one diene monomer and optionally at least one vinyl aromatic monomer.

4. The functionalized elastomer of claim 1, wherein the living anionic elastomer is derived from at least one of isoprene and butadiene, and optionally from styrene.

5. The functionalized elastomer of claim 1, wherein the living anionic elastomer is derived from butadiene and styrene.

6. The functionalized elastomer of claim 1, wherein the polymerization terminator of formula I is propaneamide, N,N-dimethyl-3-[[3-(triethoxysilyl)propyl]thio]-.

7. The functionalized elastomer of claim 1, wherein the polymerization terminator of formula I is 2,5-pyrrolidinedione, 1-methyl-3-[[3-(triethoxysilyl)propyl]thio]-.

8. The functionalized elastomer of claim 1, wherein the polymerization terminator of formula I has the structure

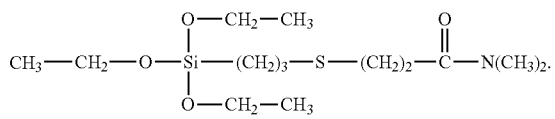

9. The functionalized elastomer of claim 1, wherein the polymerization terminator of formula I has the structure

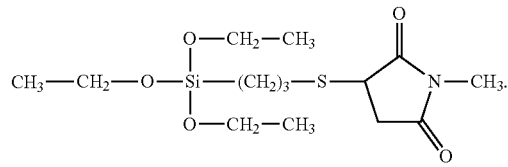

10. A rubber composition comprising the functionalized elastomer of claim 1, and further comprising silica.

11. A pneumatic tire comprising the rubber composition of claim 10.

* * * * *